(12) United States Patent
Evans et al.

(10) Patent No.: US 9,174,928 B2
(45) Date of Patent: Nov. 3, 2015

(54) PROCESS FOR IMPROVING THE SELECTIVITY OF AN EO CATALYST

(75) Inventors: Wayne Errol Evans, Richmond, TX (US); Jeffrey Michael Kobe, Houston, TX (US); Marek Matusz, Houston, TX (US)

(73) Assignee: Shell Oil Company, Houston, TX (US)

( * ) Notice: Subject to any disclaimer, the term of this patent is extended or adjusted under 35 U.S.C. 154(b) by 73 days.

(21) Appl. No.: 13/456,774

(22) Filed: Apr. 26, 2012

(65) Prior Publication Data

US 2012/0277447 A1     Nov. 1, 2012

Related U.S. Application Data

(60) Provisional application No. 61/480,581, filed on Apr. 29, 2011.

(51) Int. Cl.
*C07D 301/03*     (2006.01)
*C07C 213/04*     (2006.01)
*C07D 301/12*     (2006.01)

(52) U.S. Cl.
CPC ............ *C07C 213/04* (2013.01); *C07D 301/12* (2013.01)

(58) Field of Classification Search
None
See application file for complete search history.

(56) References Cited

U.S. PATENT DOCUMENTS

| 4,400,559 | A | 8/1983 | Bhise | |
|---|---|---|---|---|
| 4,761,394 | A | 8/1988 | Lauritzen | 502/348 |
| 4,766,105 | A | 8/1988 | Lauritzen | 502/216 |
| 4,845,296 | A | 7/1989 | Ahmed et al. | 564/477 |
| 4,874,879 | A | 10/1989 | Lauritzen et al. | 549/536 |
| 5,155,242 | A | 10/1992 | Shankar et al. | 549/534 |
| 5,380,697 | A | 1/1995 | Matusz et al. | 502/348 |
| 5,739,075 | A | 4/1998 | Matusz | 502/302 |
| 5,801,259 | A | 9/1998 | Kowaleski | 549/536 |
| 6,040,467 | A | 3/2000 | Papavassiliou et al. | 549/534 |
| 6,080,897 | A | 6/2000 | Kawabe | 568/858 |
| 6,368,998 | B1 | 4/2002 | Lockemeyer | 502/347 |

(Continued)

FOREIGN PATENT DOCUMENTS

| EP | 1532125 | 1/2004 | ........... C07D 301/10 |
|---|---|---|---|
| EP | 1458698 | 4/2005 | ........... C07D 301/10 |

(Continued)

OTHER PUBLICATIONS

Journal of the American Chemical Society 60 (1938) pp. 309-316.

(Continued)

*Primary Examiner* — Jennifer A Smith
*Assistant Examiner* — Anita Nassiri Motlagh (57) ABSTRACT

Processes for the epoxidation of ethylene are provided in which, following start-up, an epoxidation catalyst is contacted with a feed comprising ethylene, oxygen, carbon dioxide in an amount below 2.0 vol. %, and a chloride moderator to achieve a desired work rate at a first operating temperature $T_1$. The composition of the feed is subsequently adjusted (e.g., by decreasing the ethylene concentration, decreasing the oxygen concentration, increasing the carbon dioxide concentration and/or adjusting the concentration of the chloride moderator) so as to increase the first operating temperature $T_1$ to a second operating temperature $T_2$ while maintaining the desired work rate. As the catalyst activity declines, the composition of the feed is further adjusted so as to maintain the desired work rate at the second operating temperature $T_2$.

14 Claims, 2 Drawing Sheets

(56) References Cited

U.S. PATENT DOCUMENTS

| | | | |
|---|---|---|---|
| 6,372,925 B1 | 4/2002 | Evans et al. | 549/536 |
| 6,717,001 B2 | 4/2004 | Evans et al. | 549/536 |
| 7,102,022 B2 | 9/2006 | Evans et al. | 549/536 |
| 7,193,094 B2 | 3/2007 | Chipman et al. | 549/536 |
| 7,235,677 B2 | 6/2007 | Chipman et al. | 549/536 |
| 7,348,444 B2 | 3/2008 | Evans et al. | 549/534 |
| 7,485,597 B2 | 2/2009 | Lockemeyer et al. | 502/216 |
| 7,553,980 B2 | 6/2009 | Rizkalla et al. | 549/536 |
| 7,657,331 B2 | 2/2010 | Chipman et al. | 700/28 |
| 2004/0049061 A1 | 3/2004 | Lockemeyer et al. | 549/536 |
| 2004/0110971 A1 | 6/2004 | Evans et al. | |
| 2007/0129557 A1 | 6/2007 | Chipman et al. | 549/535 |
| 2009/0069583 A1 | 3/2009 | Rizkalla et al. | 549/536 |
| 2009/0082584 A1 | 3/2009 | Rizkalla et al. | |
| 2009/0234144 A1 | 9/2009 | Bos et al. | 549/534 |
| 2009/0281339 A1 | 11/2009 | Matusz et al. | 549/523 |
| 2009/0281345 A1 | 11/2009 | Matusz | |
| 2012/0136178 A1 | 5/2012 | Smaardijk et al. | |
| 2012/0149926 A1 | 6/2012 | Evans et al. | |

FOREIGN PATENT DOCUMENTS

| | | | | |
|---|---|---|---|---|
| EP | 2155708 | | 11/2008 | C07D 301/10 |
| WO | WO2004078737 | | 1/2004 | C07D 301/10 |
| WO | WO2004078736 | | 9/2004 | C07D 301/10 |
| WO | WO2007095453 | | 8/2007 | B01J 21/04 |

OTHER PUBLICATIONS

Monnier, et al., "Effects of Chlorine and Chlorine Dynamics During Silver-Catalyzed Epoxidation of Butadiene", Journal of Catalysis, Sep. 2004, vol. 226, Issue 2, pp. 321-333.

International Searching Authority report dated Jul. 18, 2012, Ref. No. TH4081-PCT, Application No. PCT/US 12/35106 filed Apr. 26, 2012.

PROCESS FOR IMPROVING THE SELECTIVITY OF AN EO CATALYST

This application claims the benefit of U.S. Provisional Application 61/480,581 filed Apr. 29, 2011, which is herein incorporated by reference.

FIELD OF THE INVENTION

The invention relates to a process for the operation of an ethylene epoxidation process which employs a silver-based highly selective epoxidation catalyst. The invention also relates to a process for the production of ethylene oxide, a 1,2-diol, a 1,2-diol ether, a 1,2-carbonate, or an alkanolamine, which process includes the improved operating method of this invention.

BACKGROUND OF THE INVENTION

In olefin epoxidation an olefin is reacted with oxygen to form an olefin epoxide, using a catalyst comprising a silver component, usually with one or more further elements deposited therewith on a support. The olefin oxide may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine.

The performance of the epoxidation process may be assessed on the basis of the selectivity, the catalyst's activity and stability of operation. The selectivity is the molar fraction of the converted olefin yielding the desired olefin oxide. Modern silver-based epoxidation catalysts are highly selective towards olefin oxide production. When using the modern catalysts in the epoxidation of ethylene the selectivity towards ethylene oxide can reach values above 85.7 mole-% at start of cycle and under favorable conditions (e.g., low work rate, low delta EO and low $CO_2$). An example of such highly selective catalysts is a catalyst comprising silver and a rhenium promoter, for example U.S. Pat. No. 4,761,394 and U.S. Pat. No. 4,766,105.

Many process improvements are known that can improve selectivity. See, e.g., U.S. Pat. No. 7,235,677; U.S. Pat. No. 7,193,094; US Pub. Pat. App. 2007/0129557; WO 2004/078736; WO 2004/078737; and EP 2,155,708. These patents also disclose that water concentration in the reactor feed should be maintained at a level of at most 0.35 mole percent, preferably less than 0.2 mole percent. Other patents disclose control of the chloride moderator to maintain good activity. See, e.g., U.S. Pat. No. 7,657,331; EP 1,458,698; and U.S. Pub. Pat. App. 2009/0069583. Still further, there are many other patents dealing with EO process operation and means to improve the performance of the catalyst in the process. See, e.g., U.S. Pat. Nos. 7,485,597, 7,102,022, 6,717,001, 7,348,444, and U.S. Pub. Pat. App. 2009/0234144.

All catalysts must first be started up in a manner to first establish a good selectivity operation. U.S. Pat. No. 7,102,022 relates to the start-up of an epoxidation process wherein a highly selective catalyst is employed. In this patent there is disclosed an improved start-up procedure wherein the highly selective catalyst is subjected to a heat treatment wherein the catalyst is contacted with a feed comprising oxygen at a temperature above the normal operating temperature of the highly selective catalyst (i.e., above 260° C.). U.S. Pub. Pat. App. 2004/0049061 relates to a method of improving the selectivity of a highly selective catalyst having a low silver density. In this document, there is disclosed a method wherein the highly selective catalyst is subjected to a heat treatment which comprises contacting the catalyst with a feed comprising oxygen at a temperature above the normal operating temperature of the highly selective catalyst (i.e., above 250° C.). U.S. Pat. No. 4,874,879 relates to the start-up of an epoxidation process employing a highly selective catalyst wherein the highly selective catalyst is first contacted with a feed containing an organic chloride moderator and ethylene, and optionally a ballast gas, at a temperature below the normal operating temperature of the catalyst. EP-B1-1532125 relates to an improved start-up procedure wherein the highly selective catalyst is first subjected to a pre-soak phase in the presence of a feed containing an organic halide and is then subjected to a stripping phase in the presence of a feed which is free of the organic halide or may comprise the organic halide in a low quantity. The stripping phase is taught to continue for a period of more than 16 hours up to 200 hours. U.S. Pat. App. No. 2009/0281339 relates to the start-up where the organic chloride in the feed is adjusted to a value sufficient to produce EO at a substantially optimum selectivity. U.S. Pat. No. 7,553,980 teaches a process for initiating a highly selective ethylene oxide catalyst in which the highly selective ethylene oxide catalyst is operated first as a 'standard' Ag-based catalyst (e.g., a catalyst that contains only silver and alkali metal, especially cesium). Moreover, the inventive initiation procedure is more efficient when the concentration of carbon dioxide in the feed is higher than 6 vol. %, and even more efficient when the concentration of carbon dioxide in the feed is higher than 10 vol. %, of the feed mixture during the initiation period.

At the end of the start-up period, the operating conditions of the plant are set to their "normal" conditions. Work rate is set to meet the production demands of the plant. The space velocity is typically set by operating the recycle gas compressor at its maximum throughput, although a lower space velocity is sometimes used to save on the cost of electricity to run the compressor. The unit pressure is usually set by the unit design and is rarely changed. The ethylene level is typically set via design constraints, the presence or absence of an ethylene recovery unit, and economic considerations. Most plants utilize some type of "flammability equation" which defines the maximum safe level of oxygen at the reactor inlet (the "flammable limit"). Based on safety concerns or past experience, the plant will define some "flammable margin" which defines how high their oxygen level is allowed to be. For example, if a plant determined that the flammable limit is 8.5%, and for safety reasons they desire a flammable margin of 0.5%, then they will operate the plant with an inlet oxygen of 8.0% or lower. Typically, a plant will operate their oxygen level as high as their flammable margin restrictions will allow. Finally, with a high-selectivity catalyst, the chloride level will be set to maximize selectivity, and it will be changed throughout life to maintain operation at a level which maximizes selectivity.

$CO_2$ levels are always present in the feed of an EO reactor, with the actual level being a function of the amount of $CO_2$ production over the catalyst, the size of the $CO_2$ absorber, and the extent to which the $CO_2$ absorber is being used. The $CO_2$ removal system is typically run as hard as possible, from the end of the start-phase through end of life, in order to minimize the $CO_2$ level at the reactor inlet. This is done because it is recognized that lower $CO_2$ levels always lead to lower reaction temperatures (at a constant production rate). Lower temperatures are commonly believed to increase the catalyst life and to improve the selectivity. These same beliefs have led plant design in recent years to have both low $CO_2$ levels and low production rates, which are the two factors that most influence reaction temperature. In the past it was common for the feed $CO_2$ level in a plant using high-selectivity catalyst to be 3% or higher; currently many EO plants operate at below 1% $CO_2$, with some plants operating below 0.3% (pushing the lower limit).

SUMMARY OF THE INVENTION

Ordinarily the operator of an EO Process plant would think that to provide maximum selectivity, they would have to utilize higher ethylene, higher oxygen, and lower $CO_2$ levels. But under the very-low-temperature conditions that can result at start-of-cycle with modern high selectivity catalyst operated in low $CO_2$ levels, that is not necessarily the case. The key finding in this invention is that the standard belief that lower temperatures improve the catalyst selectivity is not necessarily true. The invention claimed is that the "rule of thumb" stated above no longer holds in many cases. Instead, under the aforementioned low-temperature conditions, the OPTIMAL feed is a mixture that would traditionally be considered SUB-OPTIMAL, which is to say, distorted in the "wrong" direction with respect to one or more feed components. As the catalyst naturally ages and loses activity, the EO Process operator will then gradually dial back the 'distortion' in the feed mix until the parameters eventually get back to "normal", or "no longer constrained." We have shown that if a catalyst is operating at high temperatures and the temperature is reduced, a selectivity gain will be observed. But as the temperature is reduced further, the degree of selectivity gain becomes smaller, and then finally a selectivity maximum is reached. As the temperature is further decreased, selectivity also decreases. As shown in the Examples, it has been found that for certain high selectivity EO catalysts the initial operating temperature range which gives the optimum selectivity is 240 to 255° C. rather than the operating temperature of 225° C. or lower which was previously considered to be preferred.

The present invention is a method for improving the selectivity of a supported high selectivity catalyst used in the epoxidation of ethylene. The principle of the invention involves operation under constrained conditions, which is to say, operating under conditions that would have been considered non-optimal prior to the instant discovery, for an initiation period following the initial start-up of a catalyst cycle. The improved procedure is comprised of:

a. contacting a catalyst bed containing said supported high-selectivity catalyst during an initiation period following start-up with a feed gas comprising a concentration of ethylene ($E_1$), a concentration of oxygen ($O_1$), a concentration of carbon dioxide ($C_1$) below 2.0 vol. %, and a concentration of chloride moderator ($M_1$), in order to achieve the desired work rate, which will result in a first catalyst operating temperature $T_1$;

b. adjusting the feed composition by decreasing the concentration of ethylene to a new constrained level $E_2 < E_1$, and/or decreasing the concentration of oxygen to a new constrained level $O_2 < O_1$, and/or increasing the concentration of carbon dioxide to a new constrained level $C_2 > C_1$, and/or adjusting the concentration of chloride moderator to either a higher or a lower level, to drive the catalyst to a higher operating temperature $T_2$ for the specific high-selectivity catalyst while still operating at the specific desired work rate during said initiation period, wherein $T_2$ is higher than $T_1$; and c. progressively adjusting the feed composition as the catalyst activity naturally declines in order to maintain the desired workrate and the operating temperature $T_2$ by increasing the ethylene level, and/or increasing the oxygen level, and/or decreasing the carbon dioxide level, and/or adjusting the moderator composition.

It has long been held that under all circumstances, for a given high selectivity catalyst operating at a given gas space velocity and a given pressure and achieving a given work rate, adjusting feedstock concentrations to minimize the catalyst temperature would always produce the highest possible selectivity. This would mean operating at the highest concentration of ethylene and the highest concentration of oxygen allowed by the flammable limit restrictions of the particular unit, and at the lowest achievable carbon dioxide concentration, and at the selectivity-optimized moderator level that has been empirically determined. If one or more of these feed components were to be adjusted in the "wrong" direction, which is to say, if the ethylene concentration were to be decreased, and/or the oxygen concentration were to be decreased, and/or the carbon dioxide concentration were to be increased, then the catalyst temperature required to maintain the target work rate will necessarily increase from $T_1$ to some $T_2$. Prior to the discovery of the instant invention, practitioners of ethylene epoxidation would have also held that along with this inevitable increase in catalyst temperature, the observed selectivity would also inevitably decrease, even after the moderator concentration has been re-adjusted to achieve the maximum selectivity attainable at the new higher temperature $T_2$. We have discovered that contrary to this view, when plants operate at the conditions and relatively low catalyst temperature that have become increasingly commonplace during the early cycle in modern ethylene oxide plants, the maximum selectivity that can be attained is not necessarily achieved by minimizing the operating temperature. Instead, by manipulating one or more of the aforementioned feed components in the "wrong" direction to force the catalyst temperature higher in order to continue to achieve the target workrate, selectivity at the new higher temperature $T_2$ often significantly exceeds the maximum selectivity that was attainable at the initial lower temperature $T_1$.

After said new and higher selectivity has been attained by operating at the new higher temperature $T_2$, the inherent activity of the catalyst will of course slowly deteriorate over time. The usual procedure that is employed to maintain the target work rate while maintaining the best possible selectivity is to gradually increase the catalyst bed temperature, and gradually adjust upward the concentration of chloride moderator. According to the present invention, for some extended period of time it is instead preferable to maintain approximately the same catalyst temperature $T_2$, and instead compensate for the inherent deterioration of catalyst activity by gradually changing one or more of the feed components in the activity-enhancing direction, which is to say, gradually increasing the ethylene from its initial level towards the highest level that is desired, and/or gradually increasing the oxygen from its initial level toward the highest level that is allowed by flammability considerations, and/or gradually decreasing the carbon dioxide from its initial levels towards the lowest level that is ultimately desired by the plant. During the course of these changes, minor adjustments in chloride moderator may also be employed to maintain the maximum attainable selectivity under the current conditions. At some point in time, all of the feed components will have been fully adjusted to their desired levels at the catalyst temperature of $T_2$. From that point in time forward, temperature is allowed to progressively rise and moderator is progressively adjusted in the traditional manner in order to maintain the target work rate.

DETAILED DESCRIPTION OF THE INVENTION

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process. The reactor is typically equipped with heat exchange facilities to heat or cool the catalyst. As used herein, the feed composition is considered to be the composition which is contacted with the catalyst at the inlet of the catalyst bed. As used herein, the catalyst temperature or the temperature of the catalyst bed is deemed to be the weight average temperature of the catalyst particles. In most cases the reactor tubes also contain inerts at the top inlet to the tubes. Preferred inerts are Denstone® 57 and Denstone® 2000 Support Media available from Saint-Gobain NorPro. Denstone 57 contains clay and soda feldspar (which contains no less than 7% sodium oxide) in a 95:5 weight ratio. Both support media contain between 90 and 96 wt % of $Al_2O_3+SiO_2$.

When new catalysts as well as aged catalysts which, due to a plant shut-down, have been subjected to a prolonged shut-in period are utilized in the epoxidation process, it may be useful in some instances to pre-treat these catalysts prior to carrying out the start-up process by passing a sweeping gas over the catalyst at an elevated temperature. The sweeping gas is typically an inert gas, for example nitrogen or argon, or mixtures comprising nitrogen and/or argon. The elevated temperature converts a significant portion of organic nitrogen compounds which may have been used in the manufacture of the catalyst to nitrogen containing gases which are swept up in the gas stream and removed from the catalyst. In addition, any moisture may be removed from the catalyst. Typically, when the catalyst is loaded into the reactor, by utilizing the coolant heater, the temperature of the catalyst is brought up to 200 to 250° C., preferably from 210 to 230° C., and the gas flow is passed over the catalyst. Further details on this pre-treatment may be found in U.S. Pat. No. 4,874,879, which is incorporated herein by reference.

The catalyst is subjected to a start-up process which involves an initial step of contacting the catalyst with a feed comprising ethylene, oxygen, and an organic chloride. For the sake of clarity only, this step of the process will be indicated hereinafter by the term "initial start-up phase". During the initial start-up phase, the catalyst is able to produce ethylene oxide at or near the selectivity experienced after the catalyst has "lined-out" under normal initial operating conditions after the start-up process. In particular, during the initial start-up phase, the selectivity may be within 3 mole-%, more in particular within 2 mole-%, most in particular within 1 mole-% of the optimum selectivity performance under normal initial operating conditions. Suitably, the selectivity may reach and be maintained at more than 86.5 mole-%, in particular at least 87 mole-%, more in particular at least 87.5 mole-% during the initial start-up phase under representative commercial conditions (e.g., 200 kg/m³/hr, 3300 GHSV, 14.5 kPa pressure, 1 mole-% $CO_2$ at the inlet, 30 mole-% ethylene and 8 mole-% oxygen). Since the selectivity of the catalyst quickly increases, there is advantageously additional production of ethylene oxide.

During the initial start-up phase the high selectivity catalyst is subjected to a break in period. However, the fresh catalyst near the reactor inlet is often not broken in. By removing the unbroken-in high selectivity catalyst near the reactor inlet an enhanced selectivity can be obtained. This can be achieved by using broken-in high selectivity near the reactor inlet or to modify the pretreatment process to ensure that the catalyst near the reactor inlet is thoroughly heated and broken-in.

In the initial start-up phase, the catalyst is contacted with organic chloride for a period of time until an increase of at least $1\times10^{-5}$ mole-% of vinyl chloride (calculated as the moles of vinyl chloride relative to the total gas mixture) is detected in the reactor outlet or the recycle gas loop. Without wishing to be bound by theory, when using organic chlorides other than vinyl chloride, it is believed that the vinyl chloride detected in the outlet or recycle loop is generated by the reaction of surface absorbed chloride on the silver present in the catalyst with a hydrocarbon present in the feed. Preferably, the catalyst is contacted with organic chloride for a period of time until an increase of at least $2\times10^{-5}$ mole-% of vinyl chloride, in particular at most $1\times10^{-4}$ mole-%, more in particular at most $7.5\times10^{-5}$ mole-%, most in particular at most $5\times10^{-5}$ mole-% (calculated as the moles of vinyl chloride relative to the total gas mixture) is detected in the reactor outlet or the recycle gas loop. The quantity of organic chloride contacted with the catalyst may be in the range of from 1 to 12 millimolar (mmolar) equivalent of chloride per kilogram of catalyst. The mmolar equivalent of chloride is determined by multiplying the mmoles of the organic chloride by the number of chloride atoms present in the organic chloride molecule, for example 1 mmole of ethylene dichloride provides 2 mmolar equivalent of chloride. The organic chloride may be fed to the catalyst bed for a period of time ranging from 1 to 15 hours, preferably 2 to 10 hours, more preferably from 2.5 to 8 hours. Suitably, the quantity of the organic chloride contacted with the catalyst may be at most 6 mmolar equivalent/kg catalyst, in particular at most 5.5 mmolar equivalent/kg catalyst, more in particular at most 5 mmolar equivalent/kg catalyst. The quantity of the organic chloride in the feed during the initial start-up phase may be at least $1.5\times10$ mole-%, in particular at least $2\times10$ mole-%, calculated as moles of chloride, relative to the total feed. The quantity of the organic chloride during the initial start-up phase may be at most 0.1 mole-%, preferably at most 0.01 mole-%, more preferably at most 0.001 mole-%, calculated as moles of chloride, relative to the total feed. Preferably, the initial start-up feed may comprise the organic chloride in a quantity above the optimum quantity used during the initial period of normal ethylene oxide production.

The feed during the initial start-up phase also contains ethylene. Ethylene may be present in the initial start-up feed in a quantity of at least 10 mole-%, preferably at least 15 mole-%, more preferably at least 20 mole-%, relative to the total feed. Ethylene may be present in the initial start-up feed in a quantity of at most 50 mole-%, preferably at most 45 mole-%, more preferably at most 40 mole-%, relative to the total feed. Preferably, ethylene may be present in the initial start-up feed in the same or substantially the same quantity as utilized during normal ethylene oxide production. This provides an additional advantage in that ethylene concentration does not have to be adjusted between the initial start-up phase and normal ethylene oxide production post start-up making the process more efficient.

The feed during the initial start-up phase also contains oxygen. The oxygen may be present in the initial start-up feed in a quantity of at least 1 mole-%, preferably at least 2 mole-%, more preferably at least 2.5 mole-%, relative to the total feed. The oxygen may be present in the initial start-up feed in a quantity of at most 15 mole-%, preferably at most 10 mole-%, more preferably at most 5 mole-%, relative to the total feed. It may be advantageous to apply a lower oxygen quantity in the initial start-up feed, compared with the feed composition in later stages of the process during normal ethylene oxide production since a lower oxygen quantity in the feed will reduce the oxygen conversion level so that, advantageously, hot spots in the catalyst are better avoided and the process will be more easily controllable.

In an embodiment, the initial start-up phase also contains less than 2 mole-%, preferably less than 1.5 mole percent, more preferably less than 1.2 mole percent, most preferably less than 1 mole percent, in particular at most 0.75 mole percent carbon dioxide, relative to the total feed. In the normal practice of the present invention, the quantity of carbon dioxide present in the reactor feed is at least 0.1 mole percent, or at least 0.2 mole percent, or at least 0.3 mole percent, relative to the total feed. Suitably, the carbon dioxide may be present in the initial start-up feed in the same or substantially the same quantity as utilized during normal ethylene oxide production.

The balance of the feed during the initial start-up phase may also contain an inert and/or saturated hydrocarbon. The inert and saturated hydrocarbons are described hereinafter. These additional feed components are also termed hydrocarbon co-moderators, since they have an impact on the effect of the chloride moderator.

During the initial start-up phase, the catalyst temperature will be adjusted to achieve a target work rate of production. The initial start-up phase typically lasts from 15 to 400 hours after the addition of oxygen to the feed.

The reactor inlet pressure may be at most 4000 kPa absolute, preferably at most 3500 kPa absolute, more preferably at most 2500 kPa absolute. The reactor inlet pressure is at least 500 kPa absolute. The Gas Hourly Space Velocity or "GHSV", defined hereinafter, may be in the range of from 500 to 10000 Nl/(l. h).

During the initial start-up phase, the catalyst may first be contacted with a feed comprising ethylene and optionally a saturated hydrocarbon, in particular ethane and optionally methane. The organic chloride may then be added to the feed. The oxygen may be added to the feed simultaneously with or shortly after the first addition of the organic chloride to the feed. Within a few minutes of the addition of oxygen, the epoxidation reaction can initiate. Carbon dioxide and additional feed components may be added at any time, preferably simultaneously with or shortly after the first addition of oxygen to the initial start-up feed. As discussed above, during the initial start-up phase, the catalyst is able to produce ethylene oxide at or near the selectivity experienced after the catalyst has "lined-out" under normal initial operating conditions after the start-up process. During the initial start-up phase, the catalyst is operated under conditions such that ethylene oxide is produced at a level that is from 45 to 75% of the targeted production level during normal ethylene oxide production, in particular from 50 to 70%, same basis.

After the initial start-up phase, the quantity of organic chloride in the feed is adjusted to a value which is practical for the production of ethylene oxide at substantially optimum selectivity, in particular adjusted to a quantity that is within 25% of the optimum quantity of organic chloride that produces the optimum selectivity under normal initial ethylene oxide production conditions, more in particular within 10% of the optimum quantity, and most in particular adjusted to the optimum quantity of organic chloride that produces the optimum selectivity under normal initial ethylene oxide production conditions. For the sake of clarity only, this phase of the epoxidation process, i.e., the phase of the start-up process in which the organic chloride is adjusted to obtain an optimal level of selectivity for normal initial ethylene oxide production, will be indicated herein by the term "start-up adjustment phase". The optimum quantity of organic chloride at this stage is termed "$M_1$". The conditions may be changed during the adjustment phase such that the catalyst is operated under conditions such that ethylene oxide is produced at a level that is from 90 to 100% of the targeted production level during normal ethylene oxide production, in particular from 95 to 100%, same basis.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes, high-purity (at least 95 mole-%) or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The organic chloride for use in the present process may be chlorohydrocarbons. Preferably, the organic chloride is selected from the group of methyl chloride, ethyl chloride, ethylene dichloride, vinyl chloride or a mixture thereof. Most preferred reaction modifiers are ethyl chloride, vinyl chloride and ethylene dichloride.

In addition to ethylene, oxygen and the organic chloride, the production feed during the normal epoxidation process may contain one or more optional components, such as carbon dioxide, inert gases and saturated hydrocarbons.

Carbon dioxide is a by-product in the epoxidation process. However, carbon dioxide generally has an adverse effect on the catalyst activity, and high concentrations of carbon dioxide returning to the catalyst bed via the recycle loop are therefore typically avoided. A typical epoxidation reactor feed during the normal epoxidation process may contain a quantity of carbon dioxide in the feed of at most 10 mole-%, relative to the total feed, preferably at most 2 mole-%, relative to the total feed. The present invention is particularly suitable when the level of carbon dioxide of less than 2 mole-%, and preferably less than 1 mole-%, relative to the total feed, may be employed.

The inert gas may be, for example, nitrogen or argon, or a mixture thereof. Suitable saturated hydrocarbons are propane and cyclopropane, and in particular methane and ethane. Saturated hydrocarbons may be added to the feed in order to increase the oxygen flammability limit.

In the normal ethylene oxide production phase, the invention may be practiced by using methods known in the art of epoxidation processes. For further details of such epoxidation methods reference may be made, for example, to U.S. Pat. No. 4,761,394, U.S. Pat. No. 4,766,105, U.S. Pat. No. 6,372,925, B1 U.S. Pat. No. 4,874,879, and U.S. Pat. No. 5,155,242, which are incorporated herein by reference.

The key to the present invention is to establish a set of operating conditions that allows the target production rate to be achieved at maximum selectivity. If the plant were to be operated at a "typical" or "traditional" set of conditions, a catalyst temperature might result that is not appropriate for achieving maximum selectivity. Conventional wisdom holds that as operating temperature becomes progressively lower, the inherent selectivity toward EO production becomes progressively higher (all other parameters being approximately the same). According to experimental data presented herein, it has been discovered that the rate of selectivity improvement, as temperature is reduced, becomes progressively less as a catalyst temperature of about 230-235° C. is approached, and if temperature is reduced even further, selectivity begins to decrease with additional reductions in catalyst temperature. This surprising trend is in direct conflict with conventional wisdom, and has significant commercial implications. Preferably the operating temperature of the catalyst is in the range from 240 to 255° C., in order to achieve optimal selectivity toward EO production. This initial operating temperature may be different for different catalysts. As shown in Example 1, the optimum initial operating temperature for Catalyst A was between 240 and 245° C., while the optimum initial operating temperature for Catalyst B in Example 2 was between 240 and 250° C.

In the present invention, the first operating temperature $T_1$ is typically about 230° C. The substantially optimum operating temperature $T_2$ is higher than $T_1$, preferably about 5 to about 30° C. higher than $T_1$. By appropriately reducing the ethylene content in the feed mixture, reducing the oxygen in the feed mixture, and/or increasing the carbon dioxide concentration in the feed mixture, the temperature of operation to achieve the same target workrate will be increased preferably by about 5 to about 30° C. As the catalyst gradually loses some inherent activity, the feed mixture can gradually and progressively be adjusted by increasing the ethylene content, increasing the oxygen content, and/or decreasing the carbon dioxide concentration.

In the normal ethylene oxide production phase, the concentration of the components in the feed may be selected within wide ranges, as described hereinafter.

The quantity of ethylene present in the production feed may be selected within a wide range. The quantity of ethylene present in the feed will be at most 80 mole-%, relative to the total feed. Preferably, it will be in the range of from 0.5 to 70 mole-%, in particular from 1 to 60 mole-%, on the same basis. Preferably, the quantity of ethylene in the production feed is substantially the same as used in the start-up process. If desired, the ethylene concentration may be increased during the lifetime of the catalyst, by which the selectivity may be improved in an operating phase wherein the catalyst has aged, see U.S. Pat. No. 6,372,925 B1 which methods are incorporated herein by reference.

Most modern plants operate using methane ballast. In some plants, ethane is found in the feed at levels ranging from about zero up to as much as 2 vol % and higher. The levels of these saturated hydrocarbons that are present influence the level of chloride moderator that must be included in the feed stream in order to maintain optimal selectivity.

The quantity of oxygen present in the production feed may be selected within a wide range. However, in practice, oxygen is generally applied in a quantity which avoids the flammable regime. The quantity of oxygen applied will be within the range of from 4 to 15 mole-%, more typically from 5 to 12 mole-% of the total feed.

In order to remain outside the flammable regime, the quantity of oxygen present in the feed may be lowered as the quantity of ethylene is increased. The actual safe operating ranges depend, along with the feed composition, also on the reaction conditions such as the reaction temperature and the pressure.

The organic chlorides are generally effective as a reaction modifier when used in small quantities in the production feed, for example up to 0.1 mole-%, calculated as moles of chloride, relative to the total production feed, for example from $0.01 \times 10^{-4}$ to 0.01 mole-%, calculated as moles of chloride, relative to the total production feed. In particular, it is preferred that the organic chloride may be present in the feed in a quantity of from $1 \times 10^{-4}$ to $50 \times 10^{-4}$ mole-%, in particular from $1.5 \times 10^{-4}$ to $25 \times 10^{-4}$ mole-%, more in particular from $1.75 \times 10^{-4}$ to $20 \times 10^{-4}$ mole-%, calculated as moles of chloride, relative to the total production feed. Inert gases, for example nitrogen or argon, may be present in the production feed in a quantity of 0.5 to 90 mole-%, relative to the total feed. In an air based process, inert gas may be present in the production feed in a quantity of from 30 to 90 mole-%, typically from 40 to 80 mole-%. In an oxygen-based process, inert gas may be present in the production feed in a quantity of from 0.5 to 30 mole-%, typically from 1 to 15 mole-%. If saturated hydrocarbons are present, they may be present in a quantity of up to 80 mole-%, relative to the total production feed, in particular up to 75 mole-%, same basis. Frequently they are present in a quantity of at least 30 mole-%, more frequently at least 40 mole-%, same basis.

In the normal ethylene oxide production phase, the epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l. h). Preferably, the process is carried out at a work rate in the range of from 0.5 to 10 kmole ethylene oxide produced per $m^3$ of catalyst per hour, in particular 0.7 to 8 kmole ethylene oxide produced per $m^3$ of catalyst per hour, for example 5 kmole ethylene oxide produced per $m^3$ of catalyst per hour. As used herein, the work rate is the amount of ethylene oxide produced per unit volume of catalyst per hour and the selectivity is the molar quantity of ethylene oxide formed relative to the molar quantity of ethylene converted. Suitably, the process is conducted under conditions where ethylene oxide partial pressure in the product mix is in the range of from 5 to 200 kPa, for example 10 to 160 kPa, more preferably from 15 to 100 kPa. The term "product mix" as used herein is understood to refer to the product recovered from the outlet of an epoxidation reactor.

The epoxidation catalyst is a supported catalyst. The carrier may be selected from a wide range of materials. Such carrier materials may be natural or artificial inorganic materials and they include silicon carbide, clays, pumice, zeolites, charcoal, and alkaline earth metal carbonates, such as calcium carbonate. Preferred are refractory carrier materials, such as alumina, magnesia, zirconia, silica, and mixtures thereof. The most preferred carrier material is α-alumina.

The surface area of the carrier may suitably be at least 0.1 $m^2/g$, preferably at least 0.3 $m^2/g$, more preferably at least 0.5 $m^2/g$, and in particular at least 0.6 $m^2/g$, relative to the weight of the carrier; and the surface area may suitably be at most 20 $m^2/g$, preferably at most 10 $m^2/g$, more preferably at most 6 $m^2/g$, and in particular at most 4 $m^2/g$, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.42 to 0.52 g/g. A higher water absorption may be in favor in view of a more efficient deposition of the metal and promoters on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

A carrier may be washed, to remove soluble residues, before deposition of the catalyst ingredients on the carrier. Additionally, the materials used to form the carrier, including the burnout materials, may be washed to remove soluble residues. Such carriers are described in U.S. Pat. No. 6,368,998 and WO-A2-2007/095453, which are incorporated herein by reference. On the other hand, unwashed carriers may also be used successfully. Washing of the carrier generally occurs under conditions effective to remove most of the soluble and/or ionizable materials from the carrier.

The washing liquid may be, for example water, aqueous solutions comprising one or more salts, or aqueous organic diluents. Suitable salts for inclusion in an aqueous solution may include, for example ammonium salts. Suitable ammonium salts may include, for example ammonium nitrate, ammonium oxalate, ammonium fluoride, and ammonium carboxylates, such as ammonium acetate, ammonium citrate, ammonium hydrogencitrate, ammonium formate, ammonium lactate, and ammonium tartrate. Suitable salts may also include other types of nitrates such as alkali metal nitrates, for example lithium nitrate, potassium nitrate and cesium nitrate. Suitable quantities of total salt present in the aqueous solution may be at least 0.001% w, in particular at least 0.005% w, more in particular at least 0.01% w and at most 10% w, in particular at most 1% w, for example 0.03% w. Suitable organic diluents which may or may not be included are, for example, one or more of methanol, ethanol, propanol, isopropanol, tetrahydrofuran, ethylene glycol, ethylene glycol dimethyl ether, diethylene glycol dimethyl ether, dimethylformamide, acetone, or methyl ethyl ketone.

The preparation of the silver catalyst is known in the art and the known methods are applicable to the preparation of the catalyst which may be used in the practice of the present invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. No. 5,380,697, U.S. Pat. No. 5,739,075, U.S. Pat. No. 4,766,105, and U.S. Pat. No. 6,368,998, which are incorporated herein by reference. Suitably, silver dispersions, for example silver sols, may be used to deposit silver on the carrier. In an embodiment an improved reactor system is accomplished by loading at least two different catalysts having different silver density expressed as mass of silver/volume (kg Ag/m$^3$). The different silver densities can be accomplished by using catalysts with different pellet geometries (for example a solid and hollow cylinder or cylinders with different wall thickness). Another suitable way of changing silver density is to use catalysts with different silver content. Suitable range of silver contents might be from about 8% to about 50%. Such catalysts having different silver densities are then loaded into a tubular reactor in two separate layers, where one catalyst is loaded to fill from about 10% to 90% volume of the reactor and the second catalyst is loaded on top to fill the remaining volume of the reactor. Thus, an improved EO reactor system is accomplished by altering the catalyst shape density and active metal loading to achieve an optimal silver distribution in the catalyst bed. The improved reactor system results in better selectivity and productivity.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg, for example 100 to 400 g/kg. As used herein, unless otherwise specified, the weight of the catalyst is deemed to be the total weight of the catalyst including the weight of the carrier and catalytic components.

The catalyst for use in the present invention additionally comprises a rhenium promoter component. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The rhenium promoter may be present in a quantity of at least 0.01 mmole/kg, preferably at least 0.1 mmole/kg, more preferably at least 0.5 mmole/kg, most preferably at least 1 mmole/kg, in particular at least 1.25 mmole/kg, more in particular at least 1.5 mmole/kg, calculated as the total quantity of the element relative to the weight of the catalyst. The rhenium promoter may be present in a quantity of at most 500 mmole/kg, preferably at most 50 mmole/kg, more preferably at most 10 mmole/kg, calculated as the total quantity of the element relative to the weight of the catalyst.

In an embodiment, the rhenium promoter is present in a quantity of at least 1.75 mmole/kg, preferably at least 2 mmole/kg, calculated as the total quantity of the element relative to the weight of the catalyst. The rhenium promoter may be present in a quantity of at most 15 mmole/kg, preferably at most 10 mmole/kg, more preferably at most 8 mmole/kg, calculated as the total quantity of the element relative to the weight of the catalyst.

In an embodiment, the catalyst may further comprise a potassium promoter deposited on the carrier. The potassium promoter may be deposited in a quantity of at least 0.5 mmole/kg, preferably at least 1 mmole/kg, more preferably at least 1.5 mmole/kg, most preferably at least 1.75 mmole/kg, calculated as the total quantity of the potassium element deposited relative to the weight of the catalyst. The potassium promoter may be deposited in a quantity of at most 20 mmole/kg, preferably at most 15 mmole/kg, more preferably at most 10 mmole/kg, most preferably at most 5 mmole/kg, on the same basis. The potassium promoter may be deposited in a quantity in the range of from 0.5 to 20 mmole/kg, preferably from 1 to 15 mmole/kg, more preferably from 1.5 to 7.5 mmole/kg, most preferably from 1.75 to 10 mmole/kg, on the same basis. A catalyst prepared in accordance with the present invention can exhibit an improvement in selectivity, activity, and/or stability of the catalyst especially when operated under conditions where the reaction feed contains low levels of carbon dioxide.

The catalyst for use in the present invention may additionally comprise a rhenium co-promoter. The rhenium co-promoter may be selected from tungsten, molybdenum, chromium, sulfur, phosphorus, boron, and mixtures thereof.

The rhenium co-promoter may be present in a total quantity of at least 0.1 mmole/kg, more typically at least 0.25 mmole/kg, and preferably at least 0.5 mmole/kg, calculated as the element (i.e. the total of tungsten, chromium, molybdenum, sulfur, phosphorus and/or boron), relative to the weight of the catalyst. The rhenium co-promoter may be present in a total quantity of at most 40 mmole/kg, preferably at most 10 mmole/kg, more preferably at most 5 mmole/kg, on the same basis. The form in which the rhenium co-promoter may be deposited on the carrier is not material to the invention. For example, it may suitably be provided as an oxide or as an oxyanion, for example, as a sulfate, borate or molybdate, in salt or acid form.

In an embodiment, the catalyst contains the rhenium promoter and tungsten in a molar ratio of the rhenium promoter to tungsten of greater than 2, more preferably at least 2.5, most preferably at least 3. The molar ratio of the rhenium promoter to tungsten may be at most 20, preferably at most 15, more preferably at most 10.

In an embodiment, the catalyst comprises the rhenium promoter and additionally a first co-promoter component and a second co-promoter component. The first co-promoter may be selected from sulfur, phosphorus, boron, and mixtures thereof. It is particularly preferred that the first co-promoter comprises, as an element, sulfur. The second co-promoter component may be selected from tungsten, molybdenum, chromium, and mixtures thereof. It is particularly preferred that the second co-promoter component comprises, as an element, tungsten and/or molybdenum, in particular tungsten. The form in which the first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

In this embodiment, the first co-promoter may be present in a total quantity of at least 0.2 mmole/kg, preferably at least 0.3 mmole/kg, more preferably at least 0.5 mmole/kg, most preferably at least 1 mmole/kg, in particular at least 1.5 mmole/kg, more in particular at least 2 mmole/kg, calculated as the total quantity of the element (i.e., the total of sulfur, phosphorus, and/or boron) relative to the weight of the catalyst. The first co-promoter may be present in a total quantity of at most 50 mmole/kg, preferably at most 40 mmole/kg, more preferably at most 30 mmole/kg, most preferably at most 20 mmole/kg, in particular at most 10 mmole/kg, more in particular at most 6 mmole/kg, calculated as the total quantity of the element relative to the weight of the catalyst.

In this embodiment, the second co-promoter component may be present in a total quantity of at least 0.1 mmole/kg, preferably at least 0.15 mmole/kg, more preferably at least 0.2 mmole/kg, most preferably at least 0.25 mmole/kg, in particular at least 0.3 mmole/kg, more in particular at least 0.4 mmole/kg, calculated as the total quantity of the element (i.e., the total of tungsten, molybdenum, and/or chromium) relative to the weight of the catalyst. The second co-promoter may be present in a total quantity of at most 40 mmole/kg, preferably at most 20 mmole/kg, more preferably at most 10 mmole/kg, most preferably at most 5 mmole/kg, calculated as the total quantity of the element relative to the weight of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

In an embodiment, the catalyst comprises the rhenium promoter in a quantity of greater than 1 mmole/kg, relative to the weight of the catalyst, and the total quantity of the first co-promoter and the second co-promoter deposited on the carrier may be at most 3.8 mmole/kg, calculated as the total quantity of the elements (i.e., the total of sulfur, phosphorous, boron, tungsten, molybdenum and/or chromium) relative to the weight of the catalyst. In this embodiment, the total quantity of the first co-promoter and the second co-promoter may preferably be at most 3.5 mmole/kg, more preferably at most 3 mmole/kg of catalyst. In this embodiment, the total quantity of the first co-promoter and the second co-promoter may preferably be at least 0.1 mmole/kg, more preferably at least 0.5 mmole/kg, most preferably at least 1 mmole/kg of the catalyst.

The catalyst may preferably further comprise a further element deposited on the carrier. Eligible further elements may be one or more of nitrogen, fluorine, alkali metals, alkaline earth metals, titanium, hafnium, zirconium, vanadium, thallium, thorium, tantalum, niobium, gallium and germanium and mixtures thereof. Preferably, the alkali metals are selected from lithium, sodium and/or cesium. Preferably, the alkaline earth metals are selected from calcium, magnesium and barium. Preferably, the further element may be present in the catalyst in a total quantity of from 0.01 to 500 mmole/kg, more preferably from 0.5 to 100 mmole/kg, calculated as the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

In an embodiment, the catalyst may comprise cesium as a further element in a quantity of more than 2 mmole/kg, in particular at least 2.5 mmole/kg, more in particular at least 3 mmole/kg, calculated as the total quantity of the element relative to the weight of the catalyst. In this embodiment, the catalyst may comprise cesium in a quantity of at most 20 mmole/kg, in particular at most 15 mmole/kg, calculated as the total quantity of the element relative to the weight of the catalyst As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Ethylene oxide produced may be recovered from the product mix by using methods known in the art, for example by absorbing ethylene oxide from a reactor outlet stream in water and optionally recovering ethylene oxide from the aqueous solution by distillation. At least a portion of the aqueous solution containing ethylene oxide may be applied in a subsequent process for converting ethylene oxide into a 1,2-diol, a 1,2-diol ether, a 1,2-carbonate, or an alkanolamine, in particular ethylene glycol, ethylene glycol ethers, ethylene carbonate, or alkanol amines.

Ethylene oxide produced in the epoxidation process may be converted into a 1,2-diol, a 1,2-diol ether, a 1,2-carbonate, or an alkanolamine. As this invention leads to a more attractive process for the production of ethylene oxide, it concurrently leads to a more attractive process which comprises producing ethylene oxide in accordance with the invention and the subsequent use of the obtained ethylene oxide in the manufacture of the 1,2-diol, 1,2-diol ether, 1,2-carbonate, and/or alkanolamine.

The conversion into the 1,2-diol (i.e., ethylene glycol) or the 1,2-diol ether (i.e., ethylene glycol ethers) may comprise, for example, reacting ethylene oxide with water, suitably using an acidic or a basic catalyst. For example, for making predominantly the 1,2-diol and less 1,2-diol ether, ethylene oxide may be reacted with a tenfold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. Alternative 1,2-diol ethers may be prepared by converting ethylene oxide with an alcohol, in particular a primary alcohol, such as methanol or ethanol, by replacing at least a portion of the water by the alcohol.

Ethylene oxide may be converted into the corresponding 1,2-carbonate by reacting ethylene oxide with carbon dioxide. If desired, ethylene glycol may be prepared by subsequently reacting the 1,2-carbonate with water or an alcohol to form the glycol. For applicable methods, reference is made to U.S. Pat. No. 6,080,897, which is incorporated herein by reference.

The conversion into the alkanolamine may comprise, for example, reacting ethylene oxide with ammonia. Anhydrous ammonia is typically used to favor the production of monoalkanolamine. For methods applicable in the conversion of ethylene oxide into the alkanolamine, reference may be made to, for example U.S. Pat. No. 4,845,296, which is incorporated herein by reference. In one embodiment, the ethylene oxide is allowed to react with carbon dioxide in the presence of a carbonation catalyst, to form a reaction solution containing ethylene carbonate. This is followed by a hydrolysis step in which the reaction solution is converted into an ethylene glycol aqueous solution by hydrolyzing ethylene carbonate in the reaction solution. Following this step will be a distillation step in which purified ethylene glycol and a catalyst solution containing the carbonation catalyst are obtained from the ethylene glycol aqueous solution by distillation.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. The alkanolamine may be used, for example, in the treating ("sweetening") of natural gas.

Example 1

Example 1 illustrates the impact of temperature on the selectivity of a high selectivity EO catalyst (Catalyst A) by comparing standard test runs performed in laboratory microreactors. Catalyst A is a high selectivity catalyst having a silver content of about 13 weight percent on an alpha alumina support. Dopants include Re, W, Li and Cs.

Catalyst was operated at 205° C., 225° C., 245° C. and 265° C. in a feed mixture comprising 30% v ethylene, 8.0% v oxygen, 3.0% v carbon dioxide, small amounts of ethyl chloride moderator and nitrogen ballast. At each temperature the gas hourly space velocity was varied such that the product stream contained either 1.0% v EO, 2.0% v EO or 3.0% v EO. For all data collected, the chloride moderator has been adjusted to achieve maximum or "optimized" selectivity at the target production rate. Data from those sets where then subjected to computerized curve-fitting to allow approximation of selectivities at vanishing small or "0% EO". All selectivity data sets are displayed in FIG. 1.

Figure 1:
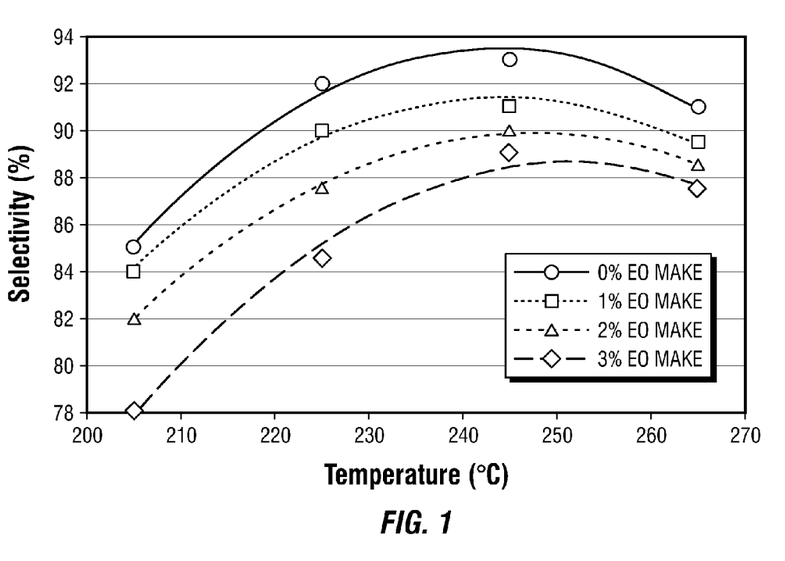
FIG. 1 depicts the relationship between selectivity and initial operating temperature for Catalyst A according to the invention.

Upon examination of FIG. 1 it is immediately apparent that as catalyst temperature was progressively reduced from 265° C. to 245° C., selectivity improved for all levels of EO production, as would be expected by the traditional understanding commonly held in the industry. However, when temperature was further reduced to 225° C., selectivity went down for each level of EO production. When temperature was further reduced to 205° C., selectivity went down yet further for each level of EO production. In FIG. 1, polynomial best-fit curves are displayed for each data set to aid in the visual analysis of the data. The well-fit curves suggest within the range of about 240-250° C., selectivity improvement as a function of reducing temperature slowed and began to reverse. Clearly, as catalyst temperatures were progressively reduced below about 240° C. selectivity loss as a function of reducing temperature became accelerated.

Example 2

Example 2 illustrates the impact of temperature on the selectivity of a different high selectivity EO catalyst (Catalyst B). Catalyst B is a high selectivity catalyst having a silver content of about 17.5 weight percent on an alpha alumina support. Dopants include Re, W, Li, and Cs. The catalyst was operated at flowrates between 33 and 539 standard cubic centimeters per minute in a feed mixture comprising 30.9% v ethylene, 7.3% v oxygen, 1.6% carbon dioxide, small amounts of ethyl chloride moderator, and nitrogen ballast. The inlet pressure was maintained at 18.1 barg. At each flowrate, the chloride moderator was adjusted to achieve maximal or "optimized" selectivity at the target production rate of 2.48% delta EO. Several flowrates were repeated, and all the selectivity-optimized data are displayed in FIG. 2.

Figure 2:
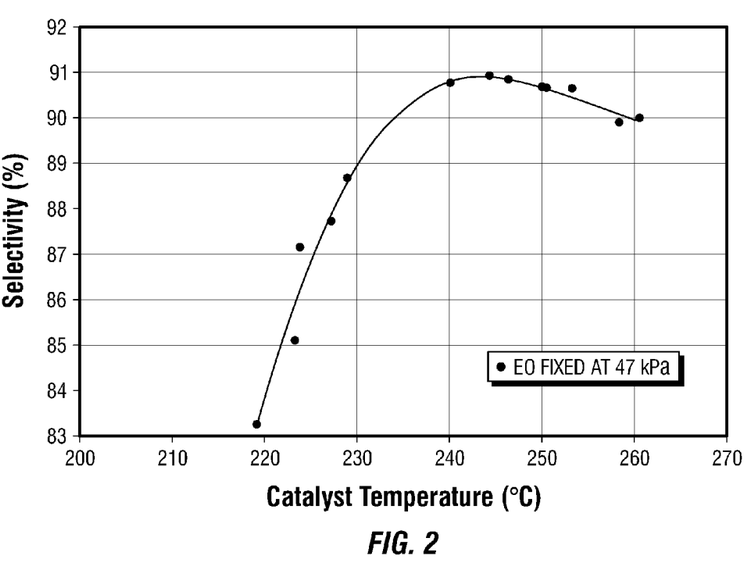
FIG. 2 depicts the relationship between selectivity and initial operating temperature for Catalyst B according to the invention.

Upon examination of FIG. 2, it is immediately apparent that as catalyst temperature was progressively reduced from about 260° C. towards 245° C., selectivity improved, as would be expected by the dogma commonly held in the industry. However, when temperature was further reduced below 245° C., selectivity decreased. In FIG. 2, a polynomial best-fit curve is displayed to aid in the visual analysis of the data. The well-fit curve suggests that within the range of about 240-250° C., a selectivity optimum was attained. Clearly, as catalyst temperatures were progressively reduced below about 240° C., selectivity loss as a function of reducing temperature became accelerated.

What is claimed is:

1. A process for the epoxidation of ethylene comprising:
   (a) following start-up, contacting an epoxidation catalyst comprising silver and a rhenium promoter with a feed composition comprising a first concentration of ethylene ($E_1$), a first concentration of oxygen ($O_1$), a first concentration of carbon dioxide ($C_1$) that is below 2.0 vol. %, and a first concentration of chloride moderator ($M_1$) to achieve a desired work rate $W_1$ at a first operating temperature $T_1$;
   (b) subsequent to step (a), adjusting the feed composition while maintaining the desired work rate $W_1$ so as to increase the first operating temperature $T_1$ to a second operating temperature $T_2$, wherein adjusting the feed composition comprises one or more of the following: (i) decreasing the first concentration of ethylene ($E_1$) to a second concentration of ethylene ($E_2$), (ii) decreasing the first concentration of oxygen ($O_1$) to a second concentration of oxygen ($O_2$), (iii) increasing the first concentration of carbon dioxide ($C_1$) to a second concentration of carbon dioxide ($C_2$), and (iv) decreasing or increasing the first concentration of the chloride moderator ($M_1$) to a second concentration of the chloride moderator ($M_2$); and
   (c) subsequent to step (b), further adjusting the feed composition so as to maintain the desired work rate $W_1$ at the second operating temperature $T_2$, wherein further adjusting the feed composition comprises one or more of the following: (i) increasing the second concentration of ethylene ($E_2$) to a third concentration of ethylene ($E_3$), (ii) increasing the second concentration of oxygen ($O_2$) to a third concentration of oxygen ($O_3$), (iii) decreasing the second concentration of carbon dioxide ($C_2$) to a third concentration of carbon dioxide ($C_3$), and (iv) increasing or decreasing the second concentration of the chloride moderator ($M_2$) to a third concentration of the chloride moderator ($M_3$).

2. The process of claim 1 wherein the rhenium promoter is present in the epoxidation catalyst in an amount greater than 1 mmole/kg, relative to the weight of the catalyst.

3. The process of claim 2 wherein the epoxidation catalyst further comprises:
   a first co-promoter selected from the group consisting of sulfur, phosphorus, boron, and mixtures thereof; and
   a second co-promoter is selected from the group consisting of tungsten, molybdenum, chromium, and mixtures thereof.

4. The process of claim 3 wherein the epoxidation catalyst further comprises a further element selected from the group consisting of fluorine, alkali metals, alkaline earth metals, titanium, hafnium, zirconium, vanadium, thallium, thorium, tantalum, niobium, gallium, germanium and mixtures thereof.

5. The process of claim 1 wherein the silver is present in the epoxidation catalyst an amount between about 150 to 500 g silver per kg catalyst.

6. The process of claim 5 wherein the epoxidation catalyst further comprises a cesium co-promoter, a lithium co-promoter and a tungsten co-promoter.

7. The process of claim 1 wherein the first operating temperature $T_1$ is less than 240° C., and the second operating temperature $T_2$ is 5 to 30° C. higher than the first operating temperature $T_1$.

8. The process of claim 6 wherein the first operating temperature $T_1$ is less than 240° C., and the second operating temperature $T_2$ is 5 to 30° C. higher than the first operating temperature $T_1$.

9. The process of claim 8 wherein the chloride moderator is selected from the group consisting of ethyl chloride, vinyl chloride, ethylene dichloride and mixtures thereof.

10. The process of claim 9 wherein the second operating temperature $T_2$ is 240 to 255° C.

11. The process of claim 9 wherein the second operating temperature $T_2$ is 240 to 250° C.

12. The process of claim 1 further comprising:
   (d) subsequent to step (c), further adjusting the feed composition so as to maintain the desired work rate $W_1$ at the second operating temperature $T_2$, wherein further adjusting the feed composition comprises adjusting the feed composition to comprise a concentration of ethylene, oxygen, carbon dioxide, and chloride moderator that is desired for non-constrained operation; and
   (e) subsequent to step (d), increasing the second operating temperature $T_2$ to a third operating temperature $T_3$.

13. The process of claim 1 further comprising:
   (d) subsequent to step (c), further adjusting the feed composition so as to maintain the desired work rate $W_1$ at the second operating temperature $T_2$, wherein further adjusting the feed composition comprises adjusting the feed composition to comprise a concentration of ethylene, oxygen, carbon dioxide, and chloride moderator that is approximately the same as the first concentration of ethylene ($E_1$), the first concentration of oxygen ($O_1$), the first concentration of carbon dioxide ($C_1$), and the first concentration of chloride moderator ($M_1$), respectively; and
   (e) subsequent to step (d), increasing the second operating temperature $T_2$ to a third operating temperature $T_3$.

14. The process of claim 2 wherein the second operating temperature $T_2$ is determined by experimentation as the temperature at which maximum selectivity is achieved for the epoxidation catalyst at the desired work rate $W_1$.

* * * * *